(12) United States Patent
Palmskog et al.

(10) Patent No.: US 8,705,029 B2
(45) Date of Patent: Apr. 22, 2014

(54) SYSTEM AND METHOD FOR DETECTION OF ANALYTES IN EXHALED BREATH

(71) Applicant: Sensa Bues AB, Huddinge (SE)

(72) Inventors: Göran Palmskog, Järfälla (SE); Olof Beck, Saltsjöö-Boo (SE); Per Ola Andersson, Umeå (SE)

(73) Assignee: Sensa Bues AB, Huddinge (SE)

( * ) Notice: Subject to any disclaimer, the term of this patent is extended or adjusted under 35 U.S.C. 154(b) by 0 days.

(21) Appl. No.: 13/739,607

(22) Filed: Jan. 11, 2013

(65) Prior Publication Data

US 2013/0128260 A1 May 23, 2013

Related U.S. Application Data

(63) Continuation of application No. 13/394,979, filed as application No. PCT/EP2010/063265 on Sep. 9, 2010, now Pat. No. 8,368,883.

(60) Provisional application No. 61/240,752, filed on Sep. 9, 2009.

(51) Int. Cl.
*G01J 3/44* (2006.01)

(52) U.S. Cl.
USPC ............................................. 356/301

(58) Field of Classification Search
USPC ................................. 356/300–301
See application file for complete search history.

(56) References Cited

U.S. PATENT DOCUMENTS

| 5,721,102 | A | 2/1998 | Vo-Dinh |
| 6,623,997 | B2 | 9/2003 | Farquharson et al. |
| 7,450,227 | B2 * | 11/2008 | Dwight et al. ............... 356/301 |
| 2006/0038990 | A1 | 2/2006 | Habib et al. |
| 2006/0084182 | A1 * | 4/2006 | Farquharson et al. ........ 436/171 |
| 2007/0258894 | A1 | 11/2007 | Melker et al. |

OTHER PUBLICATIONS

Roberta A. Sulk, Robert C. Corcoran and Keith T. Carron, Surface-Enhanced Raman Scattering Detection of Amphetamine and Methamphetamine by Modification with 2-Mercaptonicotinic Acid, Jan. 1, 1999, pp. 954-959, vol. 53, No. 8, 1999, Society for Applied Spectroscopy, Baltimore, U.S.

Bernd Sagmuller et al, Application of SERS Spectroscopy to the identification of (3,4-methylenedioxy) Amphetamine in Forensic Samples Utilizing Matrix Stabilized Silver Halides, Oct. 2001, pp. 2066-2071, vol. 126, No. 11, The Analyst, The Royal Society of Chemistry 2001.

International Search Report dated Nov. 24, 2010, in connection with related PCT/EP2010/063265 filed Sep. 9, 2010.

International Preliminary Report on Patentability dated Oct. 27, 2011, in connection with related PCT/EP2010/063265 filed Sep. 9, 2010.

* cited by examiner

*Primary Examiner* — Tara S Pajoohi Gomez
(74) *Attorney, Agent, or Firm* — Downs Rachlin Martin PLLC

(57) ABSTRACT

A device, system, and methods are disclosed for detecting the presence or determining a quantitative amount of at least one drug substance from exhaled breath of a subject in-situ. A collecting surface has a Surface Enhanced Raman Spectroscopy (SERS)-active layer that comprises at least one SERS-active material. The collecting surface is arranged as an outer surface of a waveguide for contact with exhaled breath, such that at least traces of said at least one drug substance in said exhaled breath can contact said SERS-active layer for read-out of a Raman shift spectrum that is detected in-situ for said detecting the presence or determining the quantitative amount of said at least one drug substance from said exhaled breath.

19 Claims, 9 Drawing Sheets

SYSTEM AND METHOD FOR DETECTION OF ANALYTES IN EXHALED BREATH

FIELD OF THE INVENTION

This invention pertains in general to the field of systems and methods for collecting a sample from exhaled breath of a subject, and for detecting the presence or determining the quantitative amount of analytes in the breath sample. The analytes are for instance drug substances in the exhaled breath. More particularly, the invention relates to such portable systems using Surface Enhanced Raman spectroscopy in a sensor for detecting the analytes from the exhaled breath.

BACKGROUND OF THE INVENTION

It is known that exhaled breath is commonly used in alcohol testing and today's technology makes it possible to perform on-site breath testing with legally defensible results using electrochemical sensory. An emerging technology is using infrared spectroscopy.

However, testing for other illicit drugs of abuse still requires blood or urine samples. Alternatively specimens comprising hair, sweat or oral fluid could be used. Blood sampling is invasive and requires medically trained personnel, why test subject often have to be transported to a hospital for sampling. This is time and effort consuming With long lead times the test result will be too old. Urine sampling is considered intruding on personal integrity and must be done under supervision of a nurse or a doctor. Even other issues related to samples and specimen taken from a subject to be tested arise. For instance for blood samples, and especially for urine samples are at risk of the subject exchanging the samples or using clean samples from another subject to avoid being discovered with traces of illicit drugs.

Result from a study related to this topic and performed on Ireland can be found in: Results and conclusions from Injury Prevention 2006; 12:404-408. doi: 10.1136/ip.2006.013177.33.1% of the drivers under the legal limit for alcohol tested positive for one or more of the relevant drugs, and the corresponding figures of drivers over the limit was 14.2. Among drivers who had minimal blood alcohol levels, 67.9% were taking at least one type of drug. The prevalence of taking drugs reduced steadily as alcohol concentrations increased, but still remained as high as 11.1% for drivers with blood alcohol concentrations 0.200 mg/100 ml. Being under the limit for alcohol, stopped in a city area, stopped between 6 am and 4 pm, or 4 pm and 9 pm, and being of a younger age were each independently associated with drug positivity.

Conclusions of the study point out the serious need for a readily available drug test in addition to today's alcohol tests. There are immediate implications for the evidential breath alcohol program and for checkpoints; in the event of a nil or low alcohol reading being obtained, a separate blood or urine specimen should be sought for analysis, which is currently non-routine. However, obtaining blood or urine specimen as a routine test for all drivers in regular traffic controls is not a feasible alternative due to the issues pointed out above.

Another investigation related to this topic is described in: Investigate of the prevalence and characteristics of abusive drug exposure among non-fatal motor vehicle driver casualties in Hong Kong. (Hong Kong Med J 2010; 16:246-51). The Setting for this study was a Designated trauma centre/regional accident and emergency department in Hong Kong. Investigated subjects were Non-fatal motor vehicle driver casualties who presented to the trauma centre from 1 Jan. 2007 to 31 Dec. 2007.

Results from drug screening that was performed in 395 injured drivers show 10% of whom tested positive for the drugs of interest. Ketamine was the most commonly detected abusive substance (found in 45% of the subjects). A significantly higher proportion of young drivers (aged <25 years) screened positive (odds ratio=2.3; 95% confidence interval, 1.0-5.2; P=0.04), with the rate being 21%.

The presence of these drugs in urine was related to the time of occurrence of the crash; those occurring between midnight and dawn revealed a trend towards a higher proportion of casualties testing drug-positive (odds ratio=2.2; 95% confidence interval, 0.9-5.3; P=0.07). There were no significant differences in the frequency of persons testing positive for the screened drugs with respect to gender, class of motor vehicle driven, or the day of the week on which the crash occurred This study further supports the urgent need for a convenient, reliable and quick detection of drugs in subjects. An apparatus, system and/or method would be advantageous which allows at least for a pre-screening of subjects to identify subjects under the influence of drugs. These subjects may then further investigated, e.g. by obtaining blood or urine specimens for analysis.

In addition, there is a need for being able to detect other molecules from exhaled breath as well. For instance biomarker compounds indicative of various kinds of diseases would be desirable to being able to detect.

However, as there are a multitude of different analytes in exhaled breath, most in very low amounts or only as traces, it is a challenge to have a measurement system or method that is sufficiently sensitive to discern between all these different analytes.

Thus, there is a need to provide a non-invasive, not-specimen based apparatus, system and/or method for detecting the presence or determining the quantitative amount of analytes, in particular at least one drug substance in a subject.

Hence, an improved apparatus, system and/or method for on-site sampling of a subject for analytes, in particular drug substances is desired. Such an apparatus, system and/or method for sampling the subject for illicit drugs of abuse and/or medical drugs would be desired. The apparatus, system and/or method should be efficient, non-bulky, user friendly both for operators and the subject. It should further be not intruding and not invasive. It should preferably be able to discern between various analytes.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device, a system, a method, a computer-readable medium, and a use of these that relates to the use of a Surface Enhanced Raman Spectroscopy (SERS)-sensor for detecting or determining a quantitative amount of an analyte, such as at least one drug substance, in exhaled breath from a subject in-situ, according to the appended patent claims.

According to one aspect of the invention, a device is provided, for detecting the presence or determining a quantitative amount of at least one drug substance from exhaled breath of a subject in-situ. The device having a light source, a light detector, at least one optical filter, and at least one waveguide, and a collecting surface having at least one Surface Enhanced Raman Spectroscopy (SERS)-active layer that comprises at least one SERS-active material. The collecting surface is arranged as an outer surface of the waveguide for contact with said exhaled breath, such that at least traces of at least one drug substance in the exhaled breath can contact at least one SERS-active layer.

The at least one waveguide is coupled to the light source and the detector is coupled to the at least one waveguide for a SERS measurement of emitted light from the SERS-active layer. Such that a fraction of the light from the light source, when sent through said waveguide, is transmitted from the waveguide at least partly through the outer surface of the at least one waveguide to the at least one SERS-active layer, and a fraction of a SERS-signal emitted the said SERS-active layer is transmitted back into the waveguide, through the filter and further to the detector, whereby a Raman shift spectrum is detectable for said in-situ detecting the presence or determining the quantitative amount of the at least one drug substance from said exhaled breath.

The described device thus comprises a sensor that is adapted to obtain at least one Surface Enhanced Raman Spectrum (SERS) from exhaled breath. At least one SERS spectrum can be used to determine the presence of at least one drug substance. Alternatively, or in addition, the device may in use determine a quantitative amount of at least one drug substance in exhaled breath.

The collecting surface covered with at least one SERS active layer is present on at least a portion of a waveguide only. In some embodiments, the SERS active layer covers the whole waveguide.

The waveguide is preferably an optical fiber, but is not limited to an optical fiber. In this case, the collecting surface is preferably a radial outside surface along a length of the fiber. The fiber can be in any shape like, straight, bent or coiled, depending on the design requirements of the system in which the sensor is used in, e.g. the total surface area needed to detect the presence of at least one drug substance in the collected exhaled breath.

The sensor is adapted to be used with exhaled breath or gases so no liquid solvent is needed to prepare samples for analysis. Hence the sensor can detect volatile and non-volatile analytes in air or exhaled breath as long as it gives rise to a SERS-signal when in close proximity to a SERS-active surface, substrate, colloid or material.

The physical processes on which the sensor is working are not entirely investigated. However, applicants believe that collected exhaled breath condensates at the SERS-surface and the small amount of water then evaporates, thus leaving thousands of analytes from the exhaled breath on the SERS-surface. These analytes then give rise to the emitted SERS spectrum when excited by a light source. In addition, or alternatively, the analytes may be part of an aerosol conveyed by the exhaled breath, which aerosol particles stick to the SERS-surface. Evaporation may also take place of aerosol, which then leaves the traces of the analytes on the SERS-surface for analysis.

The analytes are here drug substances and could be either medical drugs or illicit drugs like, amphetamine, opiates, cocaine, heroin, cannabis etc.

The device could comprise a temperature control element arranged to keep the collecting surface at a temperature lower than 37 deg C. to provide condensation of vapor in the exhaled breath.

In one embodiment of the invented device the SERS-active layer is covered by a second layer of a material that is permeable or selectively permeable for the at least one drug substance.

By covering the waveguide surface with at least one SERS-active layer and then put at least one layer on top of the SERS-layers that is only permeable to a certain type of analytes, here drug substances, or a specific drug substance, only these analytes that can diffuse through the layer will interact with the at least one SERS-layer making it possible to obtain clearer spectra with less obstacles from other analytes that could for example hide important peaks useful when identifying different types of drug substances.

Different areas with a SERS-active layer and different layers for selective diffusion of pre-defined analytes may be provided in a single waveguide.

The permeable layers could be selected from the group comprising silicone polymers and silica and silicone elastomers.

In another embodiment of the invented device, at least one of the at least one SERS-active layer is a mixture comprising of at least one SERS-active material and at least one material selected from the group comprising silicone elastomers, silicone polymers and silica.

Here a slurry or a mixture of the SERS-active material and at least one permeable or selectively permeable material is made and used as a layer around the waveguide. By doing this the layer will be both selective to certain drug substances and work as a SERS-active layer. This will also make the SERS-active layer easier to apply to the fiber and more resistant.

In yet another embodiment of the invented device, the SERS-active layers have a thickness less than 200 μm, preferably less than 100 μm, more preferably less than 50 μm, further more preferably less than 20 μm. The layers of drug permeable material, if applied, will have a thickness less than 200 μm, preferably less than 100 μm, more preferably less than 50 μm, further more preferably less than 20 μm.

In another embodiment of the invention device the waveguide is a sensor comprising a plurality of fibres.

Here at least two SERS-active layer covered fibres will be connected to the same at least one light source and the same detector either as a bundle or separated for example within a collection chamber. This will give a larger SERS-active area that will enhance the recorded spectra. In the case of the fibres being separated, the SERS-active area will be spread over the volume of the collection chamber so that a spectrum of a larger part of the collected volume of exhaled breath will interact with a SERS-active layer.

In another embodiment of the invented device an inlet end of a first fiber and an outlet end of a second fiber coincide at one end, and a light reflecting mirror is positioned at the first and the second fibres distal ends.

In this embodiment the light from the light source will be sent through at least one first fiber with a radial immersive SERS-active layer and then be reflected by a mirror into at least a second fiber that could have a radial immersive SERS-layer and sent to the second fibres outlet that coincides close to the first fibres inlet.

This arrangement will make it easier to have a sensor arranged inside a collection chamber for example a tube.

Another arrangement similar to the above is to have an inlet end and an outlet end, of a fiber coincide at one end of the fiber, and a light reflecting mirror is positioned at the distal end of the fiber.

This arrangement work in a similar fashion as the above described two fiber arrangement. But instead of the light being sent from the light source through one fiber and back to the detector through a second fiber, the light will in this embodiment, be sent back and forth through the same fiber. Hence the inlet, where the light is to be coupled to the fiber and the outlet where the light to be coupled from the fiber to the detector, will be the same end of the fiber.

In another embodiment of the invented device the sensor further comprises a light pulse splitter interconnected between optical fibres by means of one of a fiber optical circulator and an optical coupler.

In some embodiments the device comprises a Bragg grating for fiber spectrometer application. The object of this embodiment is to provide an improved photonic fiber detector arrangement for determining the concentration of at least one substance in a fluid, e.g. a specific substance in a specific mixture. Especially the immunity of the Bragg sensor against electric and magnetic fields may be advantageous in certain areas of application. There is no electrical energy at the site of the measurement. These sensors may be used in areas with explosive risk.

In yet another embodiment of the invented device the optical filter is used for selecting a wavelength region having peaks related to a specific type of drug substance.

By introducing different bandpass-filters between the outlet end of the waveguide and the detector it is possible to both get a higher resolution since less wavelength will be recorded on the same detector array. This will increase the possibilities of detecting a drug substance with known SERS-peaks within the wavelength range of the bandpass-filter. Multiple bandpass-filters can be used consecutive either to obtain a high resolution for a large wavelength range by adding the recording spectra or by selecting filter that each filter has a wavelength range with known peaks that can be used to characterize at least one specific drug substance.

The analytes may comprise alcohol, thus allowing for an addition of combined detection of alcohol and illicit drugs by a single device operable on site where the breath is exhaled.

According to another aspect of the invention, a system for detecting the presence or determining the quantitative amount of at least one drug substance from exhaled breath of a subject in-situ. The system comprises the invented sensor device, a collecting chamber, a mouth-piece or a breathing mask, a control unit and a user interface. The mouthpiece is arrangeable in fluid connection to the sampling chamber to direct the exhaled breath from the subject to the sampling chamber. The mouthpiece may be a unit for single use that is removable from the system. The control unit is adapted to analyze obtained spectrum and to send an indication related to a presence of a drug and/or a concentration thereof in the exhaled breath through the user-interface to the subject.

The subject will here exhale breath through the mouthpiece or mask into the collecting chamber comprising at least one inlet and one outlet. The chamber could have any size or shape but is preferably a tube. At least one SERS-sensor device is arranged inside the collecting chamber to interact with the exhaled breath. The SERS-sensor will record at least one spectrum that will be analyzed. Analysis of the spectrum may be made for example based on multivariate data analysis for example Partial Least Square (PLS), Neural Networks or fuzzy logic. The analysis is not limited to these methods since there are other methods that could be adapted to be used in embodiments of the invention by a person skilled in the art. The control unit, which carries out the analysis, may interact with the subject using a user interface. This could be by a signal like a red lamp if a drug is detected and a green lamp if the subject passes the exhaled breath test. Alternatively, or in addition, the user notification could also be a number giving the concentration in relation to for example a volume of exhaled breath and/or compared to the amount of carbon dioxide and/or water. The system could also comprise a sensor for measuring the flow of exhaled breath. This could be used to se if the right amount of exhaled breath is obtained or that the subject a breathing correctly. The preferred way is to take an extra deep breath. Since the preferred exhaled breath to measure on is the air from the lung the sensor can be used to tell the control unit when to start to measure to avoid measuring on shallow exhaled breath from the mouth and the throat.

The user interface can also be used to communicate with the user when the system is ready to be used for example after the system has stared up or initial tests have been carried out for example recording at least one background spectrum or measured against internal standards.

The invented system or SERS-sensor could be used for a wide range of applications including: detecting the presence or determining the quantitative amount of at least one drug substance from exhaled breath of a subject in-situ; such as a drug test at an emergency hospital or in an ambulance; such as at a school or a work place.

According to another aspect of the invention, a device for detecting the presence or determining a quantitative amount of an analyte, such as at least one drug substance, from exhaled breath of a subject in-situ is provided. The device comprises a light source, a light detector, and a collecting surface having at least one Surface Enhanced Raman Spectroscopy (SERS)-active layer that comprises at least one SERS-active material. The collecting surface is arranged as a surface at said device for contact with said exhaled breath, such that at least traces of said at least one drug substance in said exhaled breath can contact said SERS-active layer, and wherein said surface is arranged on top of said (SERS)-active layer or wherein said (SERS)-active layer comprises a mixture comprising at least one SERS-active material and a material that is selective permeable for said analyte. The light source and said detector are arranged to for a SERS measurement of emitted light from said SERS-active layer, such that a fraction of the light from said light source, when sent to said SERS-active layer, is transmitted at least partly through said outer surface to said at least one SERS-active layer, and a fraction of a SERS-signal emitted from said SERS-active layer is transmitted to said detector, whereby a Raman shift spectrum is detectable for said in-situ detecting the presence or determining the quantitative amount of said analyte, comprising at least one drug substance, from said exhaled breath.

This arrangement may be made planar, i.e. the collective surface is planar, receiving light from the light source and reflecting SERS-signal light back to the detector for spectral analysis.

According to yet another aspect of the invention, a method is provided for detecting the presence or determining the quantitative amount of at least one drug substance from exhaled breath of a subject in-situ. The method comprises the steps of:

providing a sensor according to the aforementioned description;

collecting an exhaled breath sample from a subject;

making contact between said exhaled breath sample and said SERS-active layer of said device;

recording at least one spectrum from light emitted from said SERS-active layer;

analyzing said at least one spectrum to detect the presence or determining the quantitative amount of at least one drug substance in said exhaled breath sample.

According to a further aspect of the invention, a method is provided, for detecting the presence or determining the quantitative amount of at least one drug substance from exhaled breath of a subject in-situ, comprising providing and using a system according to the aforementioned aspect. The method comprises the steps of:

recording at least one background spectrum using the SERS-sensor;

collecting an exhaled breath sample in a chamber;

recording a spectrum of the exhaled breath sample using said SERS-sensor;

analyzing said spectrums using the control unit; and giving said subject an indication using a user interface.

According to a further aspect of the invention, a computer-readable medium having embodied thereon a computer program for processing by a computer is provided. The computer program comprises a plurality of code segments for analyzing at least one spectrum to detect the presence or determining the quantitative amount of at least one drug substance in said exhaled breath sample.

Embodiments avoid and do not involve the use of liquid solvents for preparing the breath samples for the SERS-measurement.

Use of an SERS-active substrate or layer, or of the device, system or method of the afore mentioned aspects of the invention are provided for detecting the presence or determining the quantitative amount of analyte from exhaled breath of a subject in-situ.

The analyte may comprise at least one drug substance, and/or a biomarker compound indicative of a disease of said subject.

Use of an SERS-active substrate or layer, or of the device, system or method of the afore mentioned aspects of the invention are provided as a drug lock unit for passage systems based on exhaled breath directed onto said SERS-active substrate. A detected drug substance in exhaled breath of a subject may provide a suitable signal for a control unit of said passage system for said locking. The use may comprise locking the passage systems, such as at airports, work places, hospitals, jails, etc.

Use of an SERS-active substrate or layer, or of the device, system or method of the afore mentioned aspects of the invention are provided as a drug test at an emergency hospital or in an ambulance based on exhaled breath directed onto said SERS-active substrate.

Use of an SERS-active substrate or layer, or of the device, system or method of the afore mentioned aspects of the invention are provided as a disease diagnostic system based on exhaled breath directed onto said SERS-active substrate, wherein diagnosis of a disease of said subject is based a detected biomarker compound indicative of a disease of said subject.

Further embodiments of the invention are defined in the dependent claims, wherein features for the second and subsequent aspects of the invention are as for the first aspect mutatis mutandis.

Embodiments provide for in-situ measurements providing measurement results directly from exhaled breath.

Identification of molecules is thus detectable based on exhaled breath samples. Some embodiments allow for quantitative determination of the chemical compounds found in exhaled breath.

Some embodiments provide for sufficient sensitivity to discern between different analytes in exhaled breath samples. Measurements systems and methods that are selectively providing Raman spectra for pre-defined chemical compounds or analytes in exhaled breath are provided.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
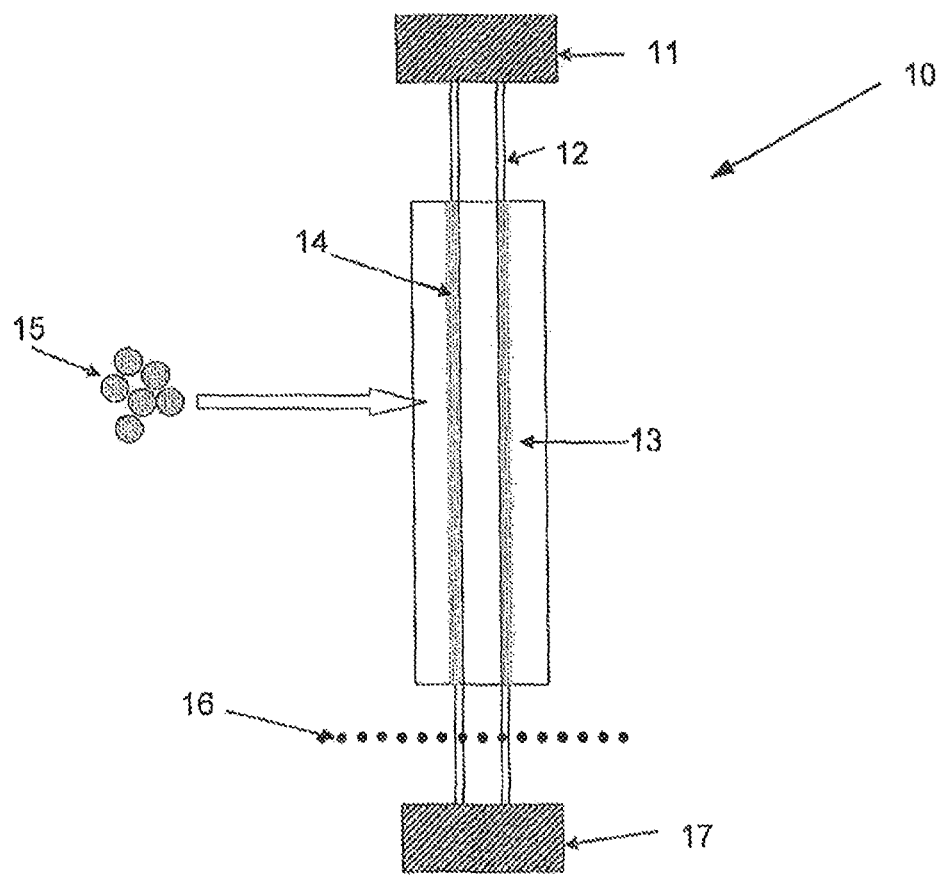
FIG. 1 is a schematic illustration that shows an embodiment of the SERS-sensor with a first SERS-active layer and an optional analyte permeable or analyte selectively permeable layer.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In an embodiment of the invention according to FIG. 1 a part of a SERS-sensor 10 is shown. The sensor 10 is based on obtaining at least one Surface Enhanced Raman Spectrum (SERS) from exhaled breath. SERS is a surface technology, described in more detail below, enhancing Raman detection technology.

Thus embodiments of the SERS sensor allow for detection of one or more substances, even when present in very low amounts or concentrations.

Returning to FIG. 1, the sensor 10 is provided in form of a waveguide 12 having at least one SERS-active layer 14. The waveguide 12 may be an optical fiber.

In the embodiment, the SERS-active layer 14 is arranged outside of the waveguide at the circumference of the waveguide 12 and is extending longitudinally along a portion of the outer surface thereof.

Each SERS-layer 14 comprises at least one SERS-active material. For each SERS-layer a different SERS-active material may be provided.

The SERS-active material should be of a metal material. The metal is preferably comprised in the group of gold or silver or copper or Platinum or palladium or any mixtures thereof. The SERS-active layer 14 could either be made of colloids or being a substrate similar to Klarite® The SERS-active material is provided as nanoparticles or nanoparticle aggregates, thus providing the SERS-active layer 14 with a nanoscale roughness.

To achieve a measurable effect by a SERS-based measurement system, as described below, a drug substance 15 found in exhaled breath needs to come into contact with the metal with a nanoscale roughness on the SERS-layer 14 surface, or with similar arrangements of the SERS active nanoparticles. The substance then determines the Raman spectrum registered by a light detector 17, which spectrum is emitted from the SERS-layer upon excitation from light of the light source 11.

The shape and size of the metal nanoparticles or nanoparticles aggregates or the roughness of the surface strongly affects the strength of the enhancement because these factors influence the ratio of absorption and scattering events.

In this embodiment a SERS-active layer 14 could optionally be at least over a surface portion thereof be covered, coated or encapsulated by an outer, encapsulating layer 13. The outer layer 13 may be made of either silicone polymers and/or silica and/or silicone elastomers or similar. The material that the encapsulating layer 13 is made of is chosen to be permeable for certain pre-defined analytes 15. The encapsulating layer 13 could therefore act as a barrier for unwanted analytes that shows a lower diffusion through the layer, thus work as a pre-selecting filter to select only the drug substances 15 of interest. Hence a clearer spectrum without unwanted peaks that could be an obstruction could be obtained. The coating 13 may reduce noise in the SERS-measurement.

Thus a SERS-sensor is provided that is configured for measurement of specific pre-defined drugs in exhaled breath, whereby the measurement is provided with an advantageous signal to noise ratio.

Figure 2:
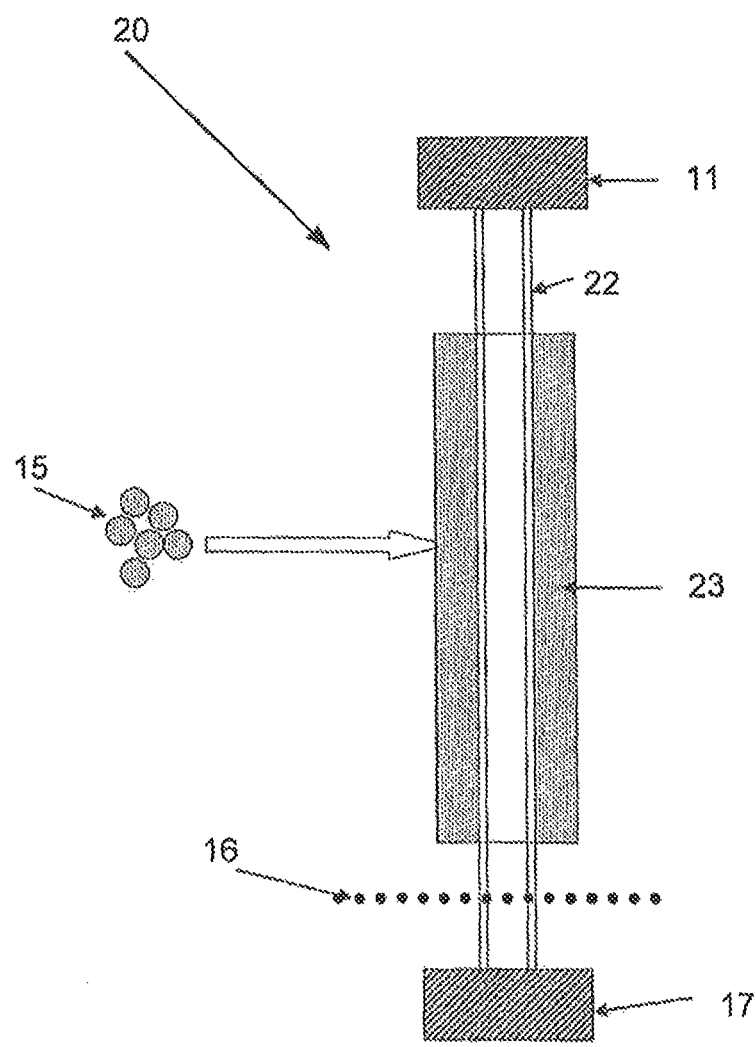
FIG. 2 is a schematic illustration that shows another embodiment of the SERS-sensor similar to the previous but with a SERS-active layer being a slurry or a mixture of at least one SERS-active material and at least on analyte permeable material.

An alternative SERS-sensor 20 is illustrated in FIG. 2. The SERS-sensor has been produced by another method for applying the SERS-material onto the waveguide-surface 22, which result can be seen in FIG. 2. Here a slurry or a mixture of the SERS-material and a selectively permeable material are provided instead of a separate SERS-active layer and a pre-selecting filter material coating. The slurry or mixture may e.g. comprise the SERS-active nanoparticles and silicone polymers and/or silica and/or silicone elastomers and are provided for use as a single layer 23 on the waveguide 22 circumference.

The waveguide 22, preferably is a fiber, as mentioned above. More preferably the fiber is a mono-mode fiber.

The waveguide 22, 12 is arranged to have an inlet connected to a light source 11. The light source 11 could here be selected from a list comprising: lasers, laser diodes, light emitting diodes, hollow cathode lamps, Xenon arc lamps, deuterium lamps, metal halide, and plasma lamps.

When a fiber is used, it could have a cladding or the SERS-active layer 14, 23 could be used as a cladding. A criterion when providing the fiber 12, 22 with a cladding layer is that light can be transmitted or coupled from the core of the fiber 12, 22 to the surrounding SERS-active layer 14, 23. The light thus diverted out of the fiber core is then provided to excite the SERS-active layer 14, 23 of the outer cladding. The emitted light from the SERS-active layer 14, 23 is then transmitted or coupled back into the same fiber 12, 22 and spectrally analyzable to provide the drug measurement result. For a Multimode or graded-index fiber 12, 22 this can be done my allowing a part of the intensity of the reflected light between the core and the cladding to transmit to the SERS-active layer 14, 23. For a mono-mode fiber 12, 22 the evanescent field could be transmitted and used to excite to the SERS-active layer 14, 23. This could for example be done by modifying the cladding either by matching the refractive index of the cladding closer to the core or by making it thinner. For some embodiments it would even be an advantage to use the SERS-active layer 14, 23 as a cladding.

The light source 11 emits preferably light in the wavelength range between 0.3 and 1.5 µm but preferably in the range 0.5-1.2 µm, and even more preferably in the range 0.75-1.1 µm.

At the opposite end of the fiber 12, 22, from the inlet, is an outlet arranged in connection to an optical filter 16 and the light is then further directed onto a detector 17.

The filter 16 is used to remove the wavelength of the light source 11. The filter 16 may in addition or alternatively be used to limit the wavelength range to include only a wavelength range with peaks known to be strong for a specific drug substance or drug substances. By putting different filters 16 between the fiber 12, 22 and the detector 17 in a sequence after each other, different parts of the wavelength range can be obtained and recorded. Wherein each wavelength range, obtained using the optical filters 16, comprises information in the form of peaks, for at least one drug substance 15. In this manner, background noise is reduced and the measurement made robust and reliable.

The detector 17 may in embodiments be selected from the list comprising: photocells, photodiodes, phototransistors, CCD, CMOS, photoelectric tubes and photomultipliers.

Figure 3:
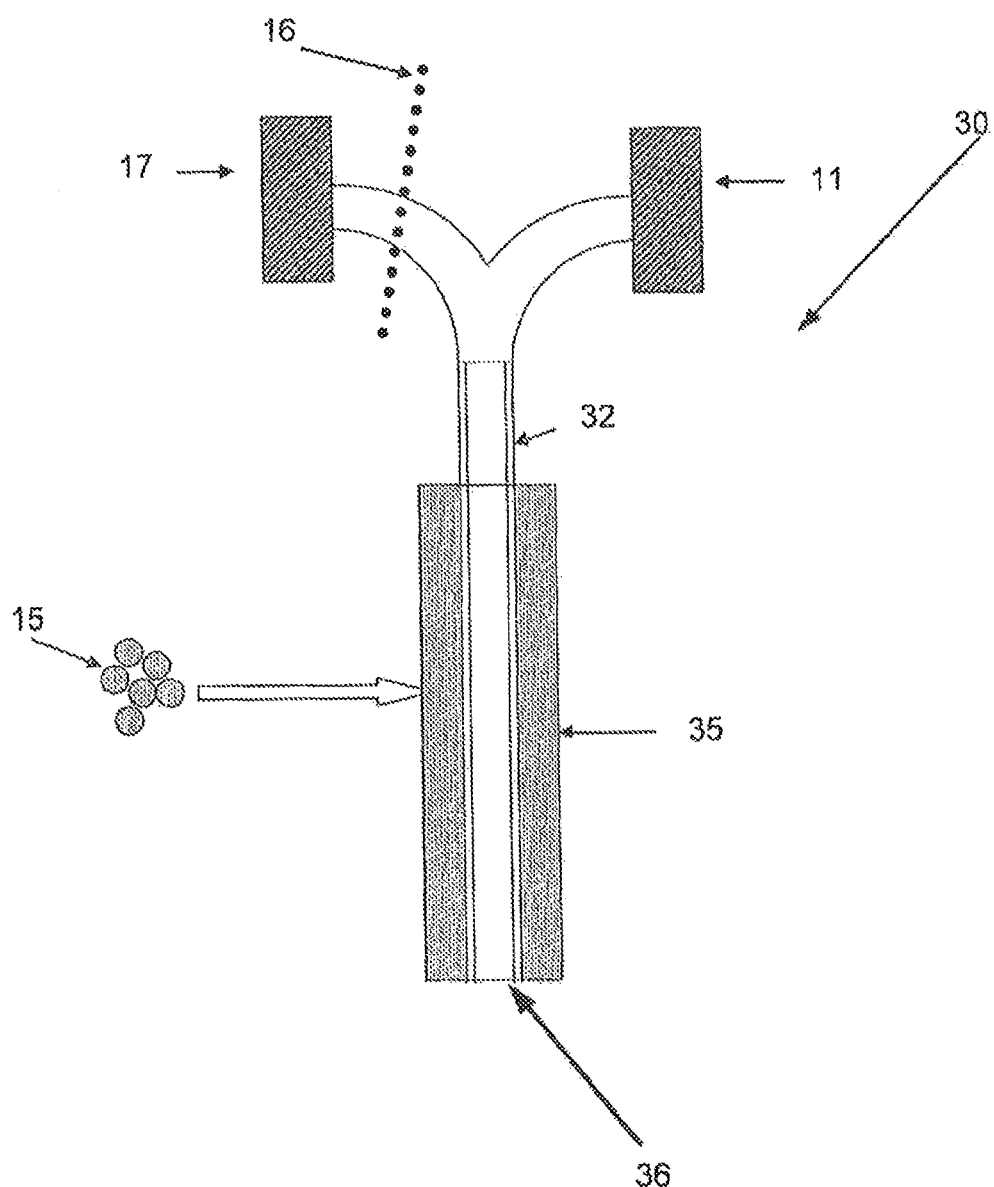
FIG. 3 is a schematic illustration that shows an alternative arrangement of the SERS-sensor.

A further embodiment of the invention is illustrated in FIG. 3 in form of a backscattering arrangement. A SERS sensor 30 is provided having one or more SERS-active layers 35. The SERS-layers 35, and if desired the drug substance permeable layers, are applied to the waveguide 32 and provided as described above. Here the detector 17, the at least one optical filter 16 and the light source 11 are located at the same side of the fiber 32 where light is both coupled in and out of the fiber 32. Thus one end of the waveguide 32 is both the excitation light inlet and the SERS layer reflected light outlet.

At the distal end of the waveguide a mirror 36 or other highly reflective material can be placed to reflect the light back into the fiber 32. This will enhance the signal further since the SERS-layer 35 will be exposed to the excitation light twice.

In some embodiments, said at least one waveguide is at least one optical fiber. The optical fiber is for instance made of silica glass or a suitable polymer. The fiber may be bent. In addition, the fiber may be coiled. Such embodiments provide for compact sensor arrangements with large available collecting surfaces.

The sensor device may comprise a plurality of fibres.

The device may further comprise a light pulse splitter interconnected between optical fibres by means of one of a fiber optical circulator and an optical coupler.

Figure 9A:
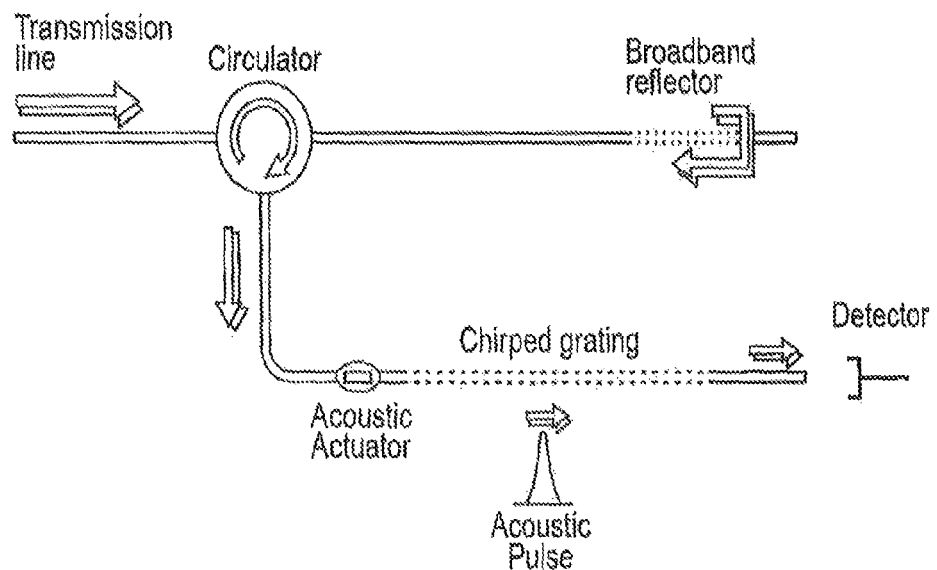
FIG. 9a is a schematic illustration of an optical filter in form of a Bragg sensor.

An example is illustrated in FIG. 9a.

In some embodiments the device comprises a Bragg grating for fiber spectrometer application.

A fiber Bragg grating (source: Wikipedia) is a type of distributed Bragg reflector constructed in a short segment of optical fiber that reflects particular wavelengths of light and transmits all others. This is achieved by adding a periodic variation to the refractive index of the fiber core, which generates a wavelength specific dielectric mirror. A fiber Bragg grating can therefore be used as an inline optical filter to block certain wavelengths, or as a wavelength-specific reflector.

The scanning filter in front of the detector is comprised of two main building blocks:

An acoustic-optic actuator device and
A fiber Bragg grating

Figure 9B:
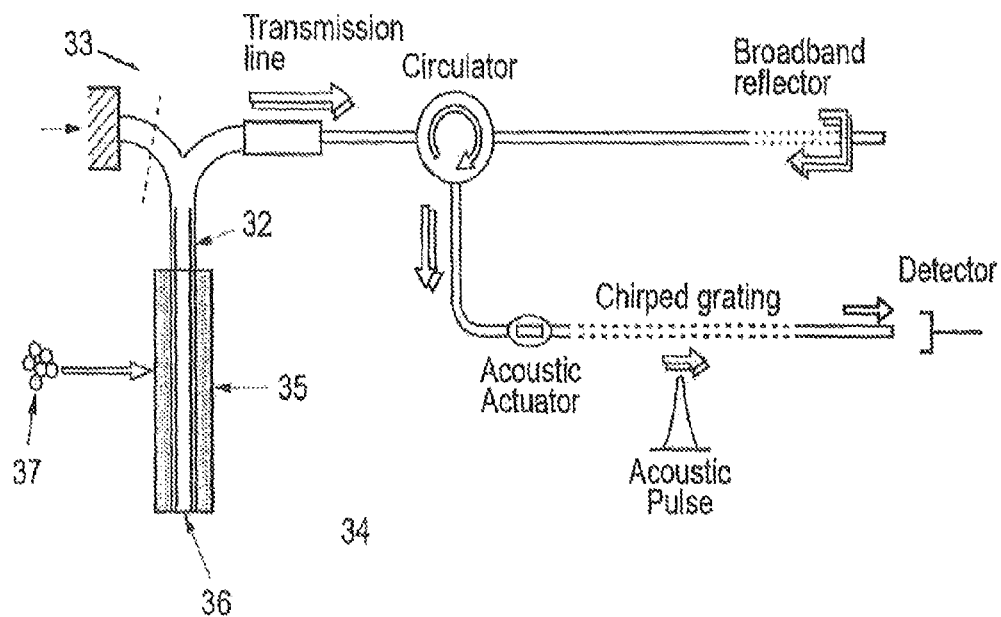
FIG. 9b is a schematic illustration illustrating an embodiment of a system based on a SERS-sensor and a Bragg sensor unit for readout.

As can be seen in FIG. 9b, a SERS-based measurement system 34, as described below, an analyte 37, such as a drug substance found in exhaled breath needs to come into contact with the metal with a nanoscale roughness on the SERS-layer 35 surface, or with similar arrangements of the SERS active nanoparticles. The substance then determines the Raman spectrum registered by a light detector, which spectrum is emitted from the SERS-layer upon excitation from light of the light source 33. A waveguide based system is shown, similar to that of FIG. 3 including a mirror 35. Instead of a filter at the detector, the Bragg grating based readout improvement is provided as describer below.

An electronic signal generator drives the acoustic actuator that launches a short, longitudinal acoustic pulse into the core of the fiber. The pulse traverses the fiber at a great speed and passes over a long, chirped fiber Bragg grating. The grating is characterized by being reflective for a certain wavelength at a well-defined position along the grating. As the acoustic pulse passes over the grating, a local and superimposed disturbance of the core's refractive index is established. By generating a disturbance of well-known character, a narrow transmission window with high sidemode suppression is created to allow a certain wavelength to pass through the grating. As the pulse moves over the chirped grating, the center wavelength of the transmission window is shifted and a scan is performed.

The Bragg based readout improvement may also be combined with other SERS sensors having different or no waveguide arrangements.

In some embodiments the collecting surface is arranged for collecting a breath condensate or aerosol with said drug. The sensor device may comprise a temperature control element that is arranged to keep said collecting surface at a temperature lower than 37 deg C. to provide condensation of vapor in said exhaled breath. Other surface parts of the sensor device may be heated to a temperature higher than 37 deg C. to avoid condensation of vapor in said exhaled breath. This allows for a controlled condensation at the collecting surface.

In another embodiment (not shown), an arrangement is provided without a waveguide having a SERS-active layer. This may be a planar arrangement of the SERS-active layer. Waveguides without SERS-active layer, such as optical fibres may be used merely for conveying light from the light source and/or to the detector.

In more detail, a device for detecting the presence or determining a quantitative amount of an analyte, such as at least one drug substance, from exhaled breath of a subject in-situ is provided. The device comprises a light source, a light detector, and a collecting surface having at least one Surface Enhanced Raman Spectroscopy (SERS)-active layer that comprises at least one SERS-active material.

The collecting surface is arranged as a surface at said device for contact with said exhaled breath, such that at least traces of said at least one drug substance in said exhaled breath can contact said SERS-active layer.

The said surface may be arranged on top of said (SERS)-active layer. Alternatively, or in addition, said (SERS)-active layer may comprise a mixture comprising at least one SERS-active material and a material that is selective permeable for said analyte.

The light source and said detector are arranged to for a SERS measurement of emitted light from said SERS-active layer, such that a fraction of the light from said light source, when sent to said SERS-active layer, is transmitted at least partly through said outer surface to said at least one SERS-active layer. A fraction of a SERS-signal emitted from said SERS-active layer is transmitted to said detector, whereby a Raman shift spectrum is detectable for said in-situ detecting the presence or determining the quantitative amount of said analyte, comprising at least one drug substance, from said exhaled breath.

This arrangement may be made planar, i.e. the collective surface is planar, receiving light from the light source and reflecting SERS-signal light back to the detector for spectral analysis.

Figure 4A:
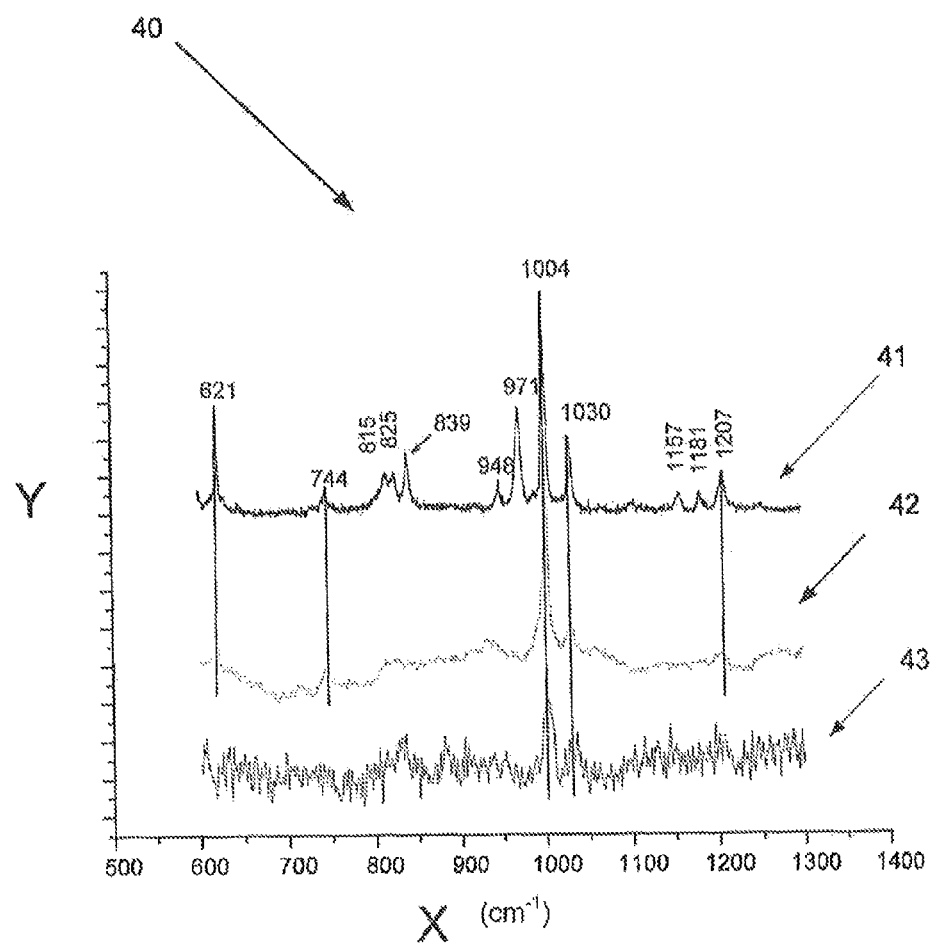
FIG. 4a is a graph that shows three Raman spectra.

In FIG. 4a, a spectrum from a test on Klarite® is shown, see the curve 42, wherein X is the wavenumber in $cm^{-1}$ and Y is The Raman intensity in cps. Klarite® substrates are commercially available from Renishaw Diagnostics, see http://www.renishawdiagnostics.com/en/12409.aspx. In more detail, the graph 40 illustrates a SERS spectrum obtained from detection of amphetamine by Raman spectroscopy utilizing irradiation light 785 nm. Normal (not enhanced) Raman spectrum of pure amphetamine powder 41 shows many peaks that can be used for identification, for example those positioned at 621, 1004, 1030 and 1207 $cm^{-1}$. SERS spectra are also obtained for diluted amphetamine solutions; one 42 corresponds to amphetamine adsorbed on gold nanostructured Klarite surface and one 43 corresponds to 1 μm amphetamine solution containing SERS active gold nanoparticles. A droplet of 2 μL amphetamine solution of 1 μM was added to Klarite surface and after solvent evaporation a laser beam was focused on a micrometer sized spot to generate a characteristic spectrum 42. The amount of the drug that gives rise to spectrum 42 is estimated to be 0.3 pg.

The SERS spectra 40 of the drug substances of FIG. 4a shows a series of unique, high intensity peaks which give a fingerprint of the molecular structure of the tested drug substance. This feature of SERS allows the identification of unknown compounds in addition to their detection at low concentrations. Furthermore, the band positions and relative intensities of the SERS-spectra match closely to the bulk Raman signal.

Surface enhanced Raman spectroscopy (SERS), is used to identify amphetamine in exhaled breath. Using the SERS surface Klarite®, measurements of very low amounts, down to a few pg, of amphetamine have successfully shown that it is possible to measure the low concentration of amphetamine expected to be found in exhaled breath. Detection of amphetamine in exhaled breath is difficult because of interfering background signals from bio molecules in breath samples and impurities in solvents. The data indicates that it is possible to measure amphetamine in exhaled air, using SERS, from drug users if it is possible to reduce the background noise.

A multivariate data analysis was used, where the first derivates of unprocessed spectra were used. Ten breath samples without amphetamine, four breath samples spiked with 20-25 pg and 2 breath samples from drug users where used to build the model. The same samples and four more samples spiked with 100 pg amphetamine were used to calculate a Partial least square (PLS) model. Results indicated clearly that multivariate data analysis is suitable for separating persons under the influence of drugs from persons not having consumed drugs.

Figure 4B:
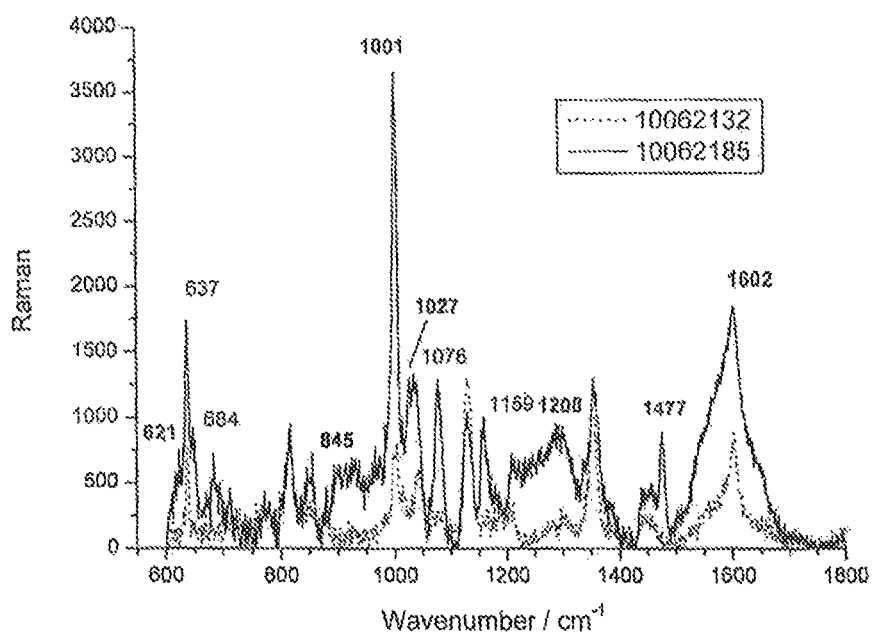
FIG. 4b is a graph that shows two SERS spectra of spiked exhaled breath, whereof one is spiked with amphetamine.

In FIG. 4b, some further SERS-spectra from a test on Klarite® are shown. The spectra shows two spectrum one of exhaled breath without amphetamine and one spiked with 20 pg. The spiked spectra has a clearly visible peaks related to amphetamine.

In FIG. 4b SERS spectra are shown of exhaled air adsorbed on a filter. Both filters where eluted with organic solvents and one of the samples where spiked with 20 pg amphetamine (red spectrum). In conjunction with SERS measurement the samples where dissolved in pure deionized water and a droplet of 2 µL was added to a naked SERS active surface (Klarite). Before laser illumination of 785 nm (3 mW) the liquid droplet was evaporated and exhaled substances were adsorbed on the SERS active surface in dry condition. The spectra were performed on a HORIBA LabRam HR800 Raman spectrometer. It is obvious the Raman signatures are of complex nature where many peaks originating from different species are overlapping. However, FIG. 4b is indicative that in principle one could distinguish between drug containing and not containing exhaled air. One way is to build up a multivariate data model where a relevant training set is crucial. Most important spectral region in such pattern recognition working model depends on the target molecules but mostly it is lying in range of 600-1800 $cm^{-1}$. Sometimes high frequency region is of importance around 2300 and 3000 $cm^{-1}$. FIG. 4b also says that it if the selectivity of the SERS surface is increased towards certain drug it should be much easier to judge any presence of target molecules. For example this could be achieved by mixing a polymeric layer with SERS active surfaces (or nanoparticles) possessing suitable physicochemical properties for diffusion certain class of analytes of interest.

FIG. 4 supports clearly the selectivity of SERS active surfaces for detecting certain chemical compounds from exhaled breath. This applies even though only very small amounts or traces of the specific compound are present in the exhaled breath. In addition, it has been shown that detection of traces of certain specific chemical compounds in exhaled breath is provided although many other chemical compounds are present in the exhaled breath and it would have been expected that measurement results were influenced. However, it was shown that measurement results for the desired specific compound under investigation are reliable and not disturbed by other compounds present in the in exhaled breath. Multiple SERS surfaces that are prepared to be selective for different chemical compounds may be combined to provide a multi parameter system in a single compact system.

Figure 5:
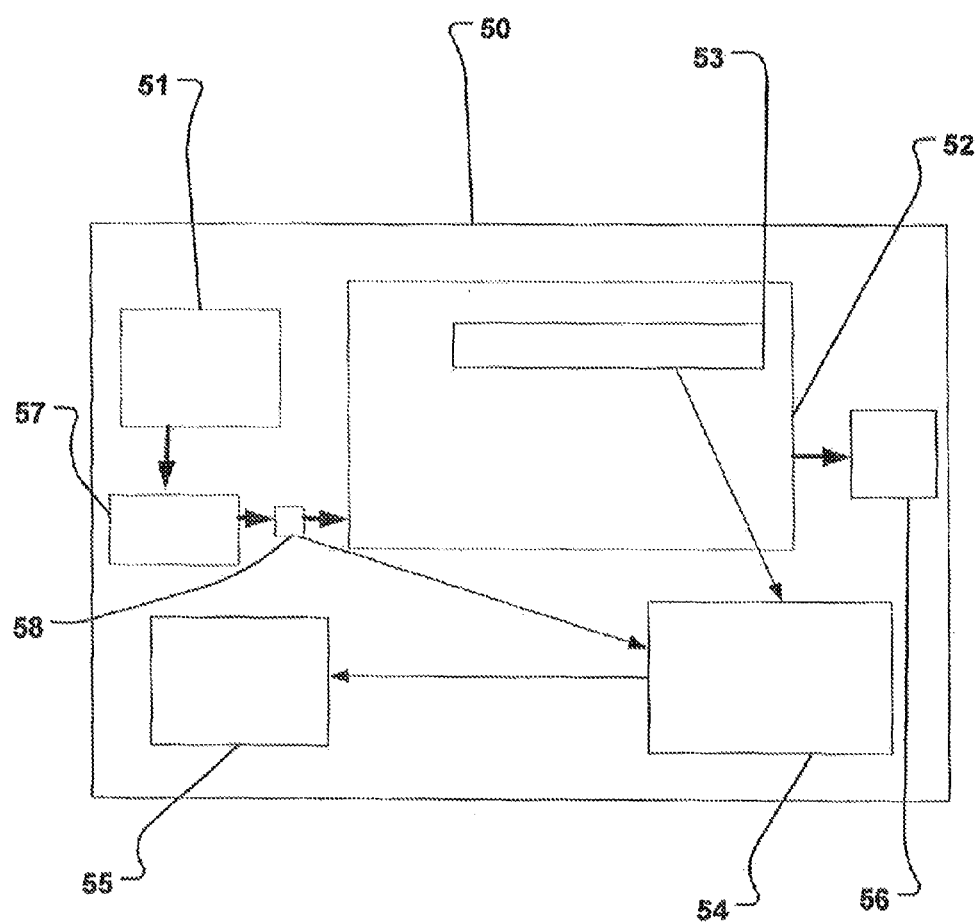
FIG. 5 is a schematic illustration illustrating an embodiment of a system based on a SERS-sensor.

FIG. 5 is a schematic chart illustrating a system 50 based on the invented sensor 53. A subject to be tested exhales into a mouth-piece or a mask 51, that is in communication with a collection chamber 52 via at least one inlet 57. The bold arrows in FIG. 5 illustrate a flow of the exhaled breath.

Optionally the inlet could be provided with a flow sensor 58 be arranged for measuring the flow of the exhaled breath and send the information to the control unit 54. Thus the flow over time and thus the volume of exhaled breath may be determined based on an output signal of the flow sensor 58. Hence, concentrations of substances in the exhaled breath may be determined In the collection chamber is at least one sensor 53 arranged for recording at least on SERS-spectrum. In use, the exhaled breath exits the chamber through the collection chamber's 52 at least one outlet 56. The at least one recorded spectrum is sent to the control unit 54 to be analyzed. The obtained result is prompted to the operator to subject via a user interface 55.

The user-interface 55 could also be used to tell the subject when the system is ready to be used or if any error has appeared, e.g. during the measurements or during the system's initialization phase.

Figure 6:
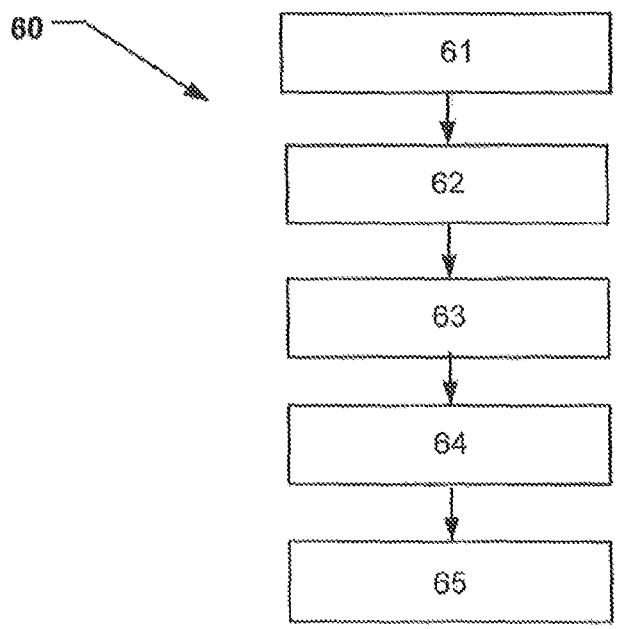
FIG. 6 is a flow-chart illustrating a first method for using a SERS-sensor.

FIG. 6 is a flow-chart illustrating the method 60 for using the SERS-sensor 61. First, the SERS-sensor 61 is provided. In the next step an exhaled breath sample is collected from a subject 62. This is done by exhaling breath onto the sensor 61. This maybe done directly or via a mouthpiece or a breathing mask. The next step is to make sure that the drug substances appears close enough 63 to the SERS-active layer so that the enhancement of the Raman spectra can occur.

It is also preferable if the exhaled breath can be in a high concentration since that will increase the concentrations of drug substance particles close to the at least one SER-active layer. This can be done by arranging the sensor 61 in a collecting chamber. When the at least one drug substance to be determined is in close proximity 63 to a SERS-active layer at least one spectrum can be recorded 64 using the sensor 61. The at least one spectrum is in use analyzed and during this analysis it can be determined if a drug substance is present and/or what drug substance is present and/or the concentration (quantitative amount) of the drug substance is determined.

Figure 7:
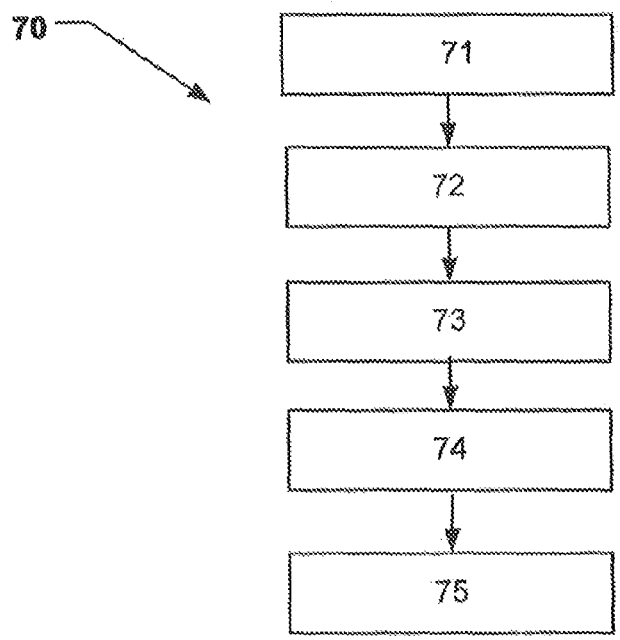
FIG. 7 is a flow-chart illustrating a second method for using a SERS-sensor system.

FIG. 7 shows a flow-chart illustrating a method 70 for detecting at least one drug substances in exhaled breath using a system comprising the aforementioned SERS-sensor.

The first step is an optional step of recording at least on background spectrum using the SERS-sensor 71.

The next step is to collect an exhaled breath sample in a collection chamber 72. The collection chamber can have any shape or size but is preferable a small tube with a small volume having the sensor arranged inside the tube. Hence there will be a high flow of exhaled breath through the tube leading to a concentration of drug particles around the sensor.

The next step is recording at least one SERS-spectrum 73 during a certain period of time. This period is determined so that a high signal-to-noise is achieved related to the time it takes for a subject to empty his/her lungs. The recorded spectrum is analyzed 74 using a software that is run on or part of a control unit 54. The Control unit is then prompting the subject with the results 75 via a user-interface. The user-interface could here be a red and a green lamp, a small display or the built in TFT screen of a passage system or a computer screen.

Figure 8:
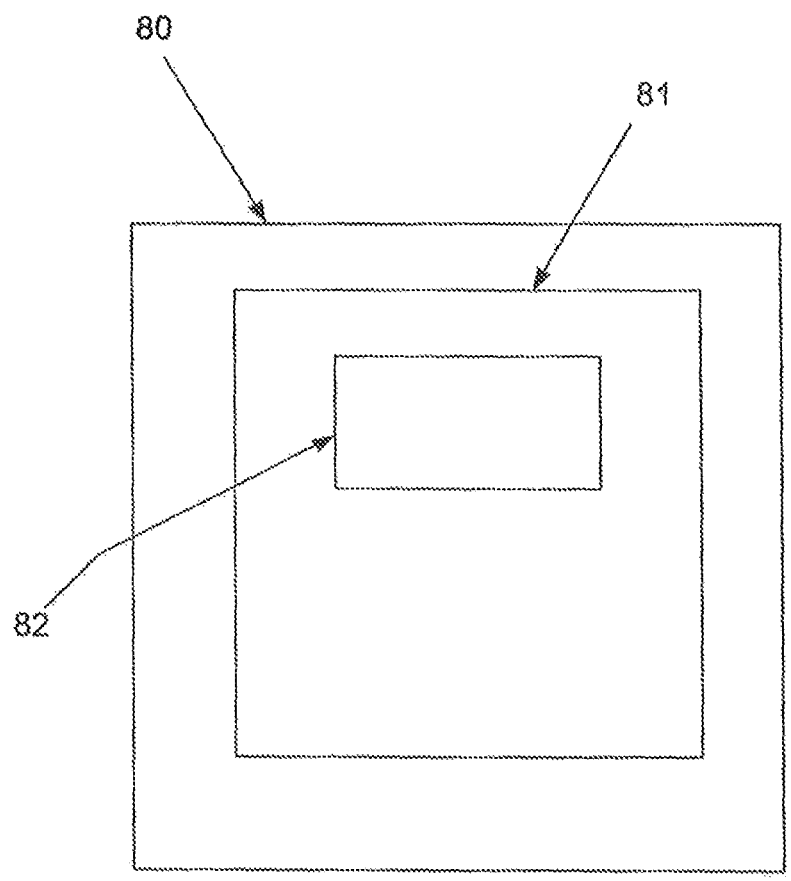
FIG. 8 is a flow-chart illustrating the code segments of a computer-program.

FIG. 8 is a flow-chart illustrating the code segments of the computer-program. 80 is a computer-readable medium with a computer program 81 having a plurality of code segments for analyzing spectral-data 82 and determining if a drug substance is presence in the exhaled breath.

The detectable drug substance may be including in the non-exhaustive list comprising Amphetamines, ecstasy, Cannabis (THC and cannabinoids), Opiates heroin/morphine, 6-AM), Cocaine, Benzodiazepines, Propoxyphene, Methadone, Buprenorphine, Tramadol, LSD, Designer/Internet drugs, Kathinon, GHB, Meprobamat, Z-drugs, Tryptamines, Anabolic steroids, Alcohol/markers but are not limited to these. Other illicit drugs not included in the list could also be detectable due to similar interchanges with the human body as the above mentioned illicit drug substances.

A practical implementation of the innovation is a handheld mobile drug testing apparatus.

The present invention has been described above with reference to specific embodiments. However, other embodiments than the above described are equally possible within the scope of the invention. Different method steps than those described above, performing the method by hardware or software, may be provided within the scope of the invention. SERS-layer described as present on the outside of waveguides may likewise be present on an interior surface of a hollow waveguide, etc. The different features and steps of the invention may be combined in other combinations than those described. The scope of the invention is only limited by the appended patent claims.

The invention claimed is:

1. A method of recovering exhaled nonvolatile drug compounds from a filter, comprising:
   providing said filter comprising an exhaled aerosol comprising said nonvolatile drug compounds;
   eluting said nonvolatile compounds from said filter with an organic solvent to form a sample;
   evaporating at least a portion of said sample on a SERS-active surface;
   recording at least one SERS-spectrum of said evaporated portion of said sample using SERS-technique.

2. The method according to claim 1, performing an analysis of the content in said sample from said at least one recorded SERS-spectrum.

3. The method according to claim 1, comprising identifying said nonvolatile drug compounds from said SERS-spectra using a multivariate data model.

4. The method according to claim 2, performing an analysis of the content in said sample from said at least one recorded SERS-spectrum.

5. The method according to claim 1, comprising facilitating analysis by modifying said SERS-active surface to be selective towards certain drug compounds.

6. The method according to claim 5, comprising mixing a polymeric layer with nanoparticles to obtain a SERS-active surface.

7. The method according to claim 5, wherein said SERS-active surface is possessing suitable physiochemical properties for diffusion certain class of drug compounds.

8. The method according to claim 5, comprising adding a permeable layer selected from a group comprising silicone polymers, silica or silicone-elastomers to said SERS-active surface.

9. The method according to claim 8, wherein said added layer is covering, coating or encapsulating said SERS-active surface.

10. The method according to claim 6, comprising adding a permeable layer selected from a group comprising silicone polymers, silica or silicone-elastomers to said SERS-active surface.

11. The method according to claim 5, comprising mixing of at least one SERS-active material and at least one material selected from a group comprising silicone elastomers, silicone polymers or silica to form said SERS-active surface.

12. The method according to claim 6, comprising mixing of at least one SERS-active material and at least one material selected from a group comprising silicone elastomers, silicone polymers or silica to form said SERS-active surface.

13. The method according to claim 1, comprising adding pure deionized water to the sample.

14. The method according to claim 1, wherein detectable nonvolatile drug compounds is included in the list comprising: Amphetamines, ecstasy, Cannabis (THC and cannabinoids), Opiates heroin/morphine, 6-AM), Cocaine, Benzodiazepines, Propoxyphene, Methadone, Buprenorphine, Tramadol, LSD, Designer/Internet drugs, Kathinon, GHB, Meprobamat, Z-drugs, Tryptamines and Anabolic steroids.

15. A non-transitory computer-readable medium comprising a computer program configured for said recording at least one SERS-spectrum according to claim 1 and said performing an analysis according to claim 2, wherein said computer program comprises code segments for:
   recording at least one SERS-spectrum according to claim 1;
   analyzing said at least one SERS spectrum according to claim 2; and
   reporting a presence or determining a quantitative amount of nonvolatile drug compounds, in said exhaled breath sample.

16. The non-transitory computer-readable medium of claim 15, further comprising a code segment for identifying said nonvolatile drug compounds from said at least one SERS-spectrum using a multivariate data model.

17. A method of detecting a nonvolatile drug compound present in exhaled breath, the exhaled breath being absorbed on a filter, the method comprising:
   eluting said nonvolatile drug compound from said filter with an organic solvent to form a sample;
   evaporating at least a portion of said sample on a SERS-active surface;
   recording at least one SERS-spectrum of said evaporated portion of said sample using SERS-technique.

18. The method of according to claim 17, further comprising capturing an exhaled aerosol from the exhaled breath in said filter.

19. The method according to claim 18, further comprising a subject exhaling into said filter.

* * * * *